United States Patent
Kärki

(10) Patent No.: US 9,039,272 B2
(45) Date of Patent: May 26, 2015

(54) CHANGING AND MEASURING CONSISTENCY

(75) Inventor: Pasi Kärki, Kajaani (FI)

(73) Assignee: METSO AUTOMATION OY, Helsinki (FI)

( * ) Notice: Subject to any disclaimer, the term of this patent is extended or adjusted under 35 U.S.C. 154(b) by 1438 days.

(21) Appl. No.: 11/887,760

(22) PCT Filed: Mar. 31, 2006

(86) PCT No.: PCT/FI2006/050120
§ 371 (c)(1),
(2), (4) Date: Jan. 14, 2008

(87) PCT Pub. No.: WO2006/106177
PCT Pub. Date: Oct. 12, 2006

(65) Prior Publication Data
US 2008/0250848 A1    Oct. 16, 2008

(30) Foreign Application Priority Data
Apr. 4, 2005 (FI) ..................................... 20055150

(51) Int. Cl.
*B01F 15/02* (2006.01)
*G01N 1/38* (2006.01)

(52) U.S. Cl.
CPC ........................................ *G01N 1/38* (2013.01)

(58) Field of Classification Search
CPC .................................................. B01F 15/0261
USPC .................. 73/61.71; 356/335, 336; 366/142, 366/154.1, 158.5, 182.4
See application file for complete search history.

(56) References Cited

U.S. PATENT DOCUMENTS

| | | | | |
|---|---|---|---|---|
| 1,985,868 A | * | 12/1934 | Maust | 106/743 |
| 2,883,343 A | * | 4/1959 | Favre et al. | 508/378 |
| 3,271,241 A | * | 9/1966 | Mumme | 162/353 |
| 3,461,030 A | | 8/1969 | Keyes | |
| 3,498,719 A | | 3/1970 | Wing et al. | |
| RE27,681 E | * | 6/1973 | Gaddis | 366/153.1 |
| 3,957,253 A | * | 5/1976 | Barton et al. | 366/132 |
| 3,972,614 A | * | 8/1976 | Johansen et al. | 356/36 |
| 3,982,126 A | * | 9/1976 | Von Alfthan | 378/47 |

(Continued)

FOREIGN PATENT DOCUMENTS

| | | |
|---|---|---|
| EP | 0 336 234 A2 | 10/1989 |
| JP | A-64-14386 | 1/1989 |
| WO | WO 03/046518 A1 | 6/2003 |

OTHER PUBLICATIONS

Jun. 7, 2011 Notification of Reasons for Rejection for Japanese Application No. 2008-504788 w/English translation.

*Primary Examiner* — David Sorkin
(74) *Attorney, Agent, or Firm* — Oliff PLC

(57) ABSTRACT

A measuring device comprising at least one mixer structure to receive a fiber suspension sample from at least one process part. Each mixer structure is provided with a measuring unit, a feeding valve for feeding feed liquid into a sample line for pushing the sample in the sample line towards the measuring unit, a mixing valve structure for feeding dilution liquid into the mixer structure The mixer structure mixes the flowing sample and the dilution liquid with one another in order to reduce the consistency of the sample. The measuring device measures from the first part of the mixed sample one property of the fiber suspension and the measuring device measures from the second part of the mixed sample a further property.

20 Claims, 5 Drawing Sheets

(56) References Cited

U.S. PATENT DOCUMENTS

Figure 1:
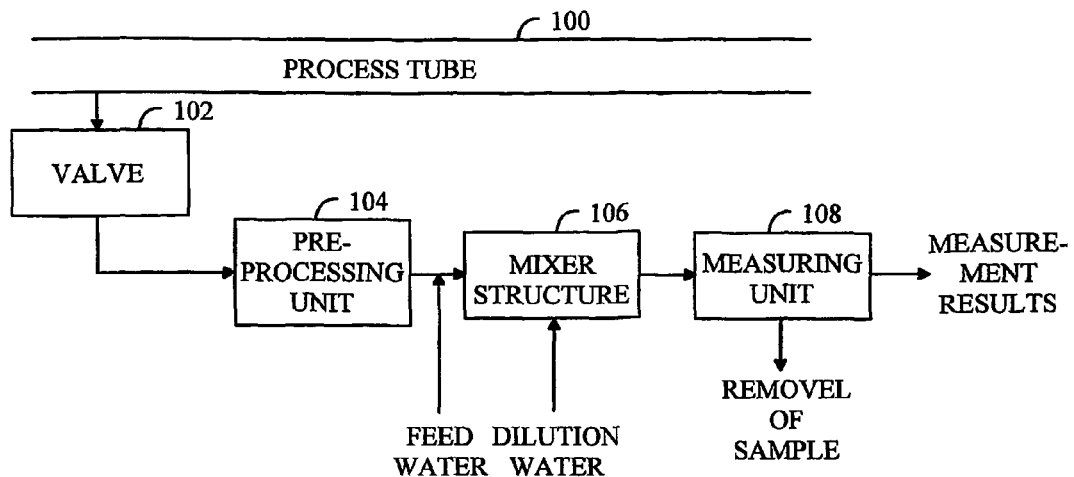

| | | | |
|---|---|---|---|
| 4,051,065 A * | 9/1977 | Venema | 366/181.5 |
| 4,178,796 A | 12/1979 | Zwicker et al. | |
| 4,220,499 A | 9/1980 | Hughes et al. | |
| 4,265,858 A * | 5/1981 | Crum et al. | 422/129 |
| 4,332,483 A * | 6/1982 | Hope et al. | 366/132 |
| 4,357,110 A * | 11/1982 | Hope et al. | 366/132 |
| 4,514,257 A * | 4/1985 | Karlsson et al. | 162/49 |
| 4,529,309 A * | 7/1985 | Pettersson et al. | 356/335 |
| 4,533,254 A * | 8/1985 | Cook et al. | 366/176.1 |
| 4,664,891 A * | 5/1987 | Cosentino et al. | 422/269 |
| 4,761,074 A * | 8/1988 | Kohsaka et al. | 356/37 |
| 4,853,945 A * | 8/1989 | Rich et al. | 377/10 |
| 5,059,349 A * | 10/1991 | Carlon et al. | 252/408.1 |
| 5,293,219 A * | 3/1994 | Ayer | 356/634 |
| 5,454,912 A | 10/1995 | Dougherty | |
| 5,460,446 A * | 10/1995 | Chevallet et al. | 366/132 |
| 5,570,953 A * | 11/1996 | DeWall | 366/10 |
| 5,786,894 A | 7/1998 | Shields et al. | |
| 5,907,108 A | 5/1999 | Garcia-Rubio et al. | |
| 5,970,805 A | 10/1999 | Foody et al. | |
| 6,412,337 B1 | 7/2002 | Arzate et al. | |
| 6,422,068 B1 * | 7/2002 | Schroder et al. | 73/61.71 |
| 6,565,755 B1 * | 5/2003 | Holdsworth | 210/709 |
| 6,703,618 B2 | 3/2004 | Karki et al. | |
| 6,799,883 B1 * | 10/2004 | Urquhart et al. | 366/152.4 |
| 2002/0003624 A1 * | 1/2002 | Yamaguchi | 356/336 |
| 2003/0030005 A1 | 2/2003 | Karki et al. | |
| 2004/0046957 A1 * | 3/2004 | Stagg | 356/335 |
| 2004/0190367 A1 * | 9/2004 | Wierzbicki et al. | 366/140 |
| 2006/0139638 A1 * | 6/2006 | Muller et al. | 356/342 |
| 2007/0295063 A1 * | 12/2007 | Cho et al. | 73/61.71 |
| 2010/0061180 A1 * | 3/2010 | Yu et al. | 366/142 |

* cited by examiner

CHANGING AND MEASURING CONSISTENCY

FIELD

The invention relates to a method and an arrangement for changing consistency and to a method and a measuring device for measuring the properties of a sample. The invention also relates to a computer program according to the method.

BACKGROUND

For instance in paper, board and pulp industry a need has arisen to carry out measurements of stock for supervising and controlling the process. Stock refers to suspension that includes liquid, particles of a solid such as fibres and possibly sticks and some gas. The idea of the measurements is to determine the properties of wood fibres to be used for making paper or board, such as length, thickness or the fibre wall thickness or other stock properties, such as freeness.

Generally the sample taken from the process is to be diluted in order to analyze it. A sample that is too consistent may cause a measuring device or an analyzer to clog up. A sample that is too consistent may also cause for instance a measurement error, if an excessive amount of individual objects, such as fibres or sticks, simultaneously fall on the observation area of the measuring device. The aim is to measure frequently from the same sample various properties of the stock or of a component thereof. Typically the different measurements are carried out for different consistencies that appropriately suit each measurement.

Typically a sample is directed from a sampler to a sample processing system, into which dilution water is conveyed. The diluted sample can be circulated in the system, which may comprise for instance a sampling vessel and/or a sampling tube system, in order to ensure the homogeneity of the sample by means of for instance a pump or a mixer. As regards the measurement quality it is generally important that an adequate amount of the undiluted sample or a component thereof is taken for analysis. The result of a minimum amount requirement of a representative sample and the dilution need of the sample is often that the sample processing system to be dimensioned in accordance with the amount of diluted sample becomes large and expensive. The use of excessive dilution liquid also increases the costs and also the environmental load. Owing to the "slowness" caused by the size and structure of the sample processing and dilution system the flow of the dilution liquid in relation to the amount of sample generally has to be kept small. This may significantly prolong the total time required for analyzing the sample.

BRIEF DESCRIPTION

It is an object of the invention to provide improved methods and a measuring device, an arrangement and a computer program implementing the methods. Thus, the invention relates to a method for changing the consistency of a sample for a process including fibre suspension. The method also comprises receiving a fibre suspension sample from at least one process part to at least one sample line, each sample line comprising feeding feed liquid into the sample line for pushing the sample forward in the sample line, feeding dilution liquid to a mixer structure and mixing the flowing sample and the dilution liquid with one another in order to reduce the consistency of the sample in the mixer structure.

The invention also relates to an arrangement for changing the consistency of a sample for a process including fibre suspension. The arrangement for changing the consistency of the sample comprises at least one mixer structure, each one of which comprising a sample line and each one being provided with a mixing valve structure for each mixer structure, and a feeding valve, and each mixer structure is arranged to receive a sample comprising fibre suspension, and in association with each mixer structure the feeding valve is arranged to feed feed liquid into the sample line for pushing the sample forward in the sample line towards the mixer structure, the mixing valve structure is arranged to feed dilution liquid into the mixer structure, the mixer structure is arranged to mix the forward flowing sample and the water fed from the mixing valve structure with one another in order to reduce the consistency of the sample.

The invention further relates to a method for measuring properties of fibre suspension in at least two consistencies. The method further comprises receiving a fibre suspension sample from at least one process part to at least one sample line, and each sample line comprising feeding feed liquid into the sample line for pushing the sample forward in the sample line, feeding dilution liquid into a mixer structure, mixing the flowing sample and the dilution liquid with one another in order to reduce the consistency of the sample in the mixer structure, measuring at least one property of the fibre suspension from the first part of the mixed sample when the sample arrives for measurement, continuing to feed feed liquid into the sample line for pushing the sample in the sample line towards the following measurement, and measuring at least one further property of the fibre suspension from a second part of the mixed sample.

The invention also relates to a measuring device for measuring properties of the fibre suspension in at least two consistencies. The measuring device comprises at least one mixer structure for receiving a fibre suspension sample from at least one process part, and each mixer structure comprises a sample line, at least one measuring unit, a feeding valve for feeding feed liquid into the sample line for pushing the sample in the sample line towards the measuring unit, a mixer structure, a mixing valve structure for feeding dilution liquid into the mixer structure for mixing the sample and the dilution liquid with one another in order to reduce the consistency of the sample, and the measuring device is arranged to measure from a first part of the mixed sample at least one property of the fibre suspension while the sample remains in the measuring unit when the feed liquid has pushed the sample to the measuring unit of the first part and the measuring device is arranged to measure from a second part of the mixed sample at least one further property of the fibre suspension while the feeding of feed liquid continues to the sample line and when the second part of the sample is pushed to a different measuring unit.

The invention further relates to a computer program for carrying out a computer process, which while running changes the consistency of a sample taken from a process including fibre suspension. The computer process comprises receiving a fibre suspension sample from at least one process part to at least one sample line, and each sample line comprises feeding feed liquid into the sample line for pushing the sample forward in the sample line, feeding dilution liquid into a mixer structure and mixing the flowing sample and the dilution liquid with one another in order to reduce the consistency of the sample in the mixer structure.

The preferred embodiments of the invention are disclosed in the dependent claims.

The method and the arrangement of the invention provide several advantages. The structure of the arrangement is simple and small in size and therefore advantageous to produce. The consistency is accurately and rapidly controlled. The need for dilution liquid is insignificant.

LIST OF DRAWINGS

Figure 2:
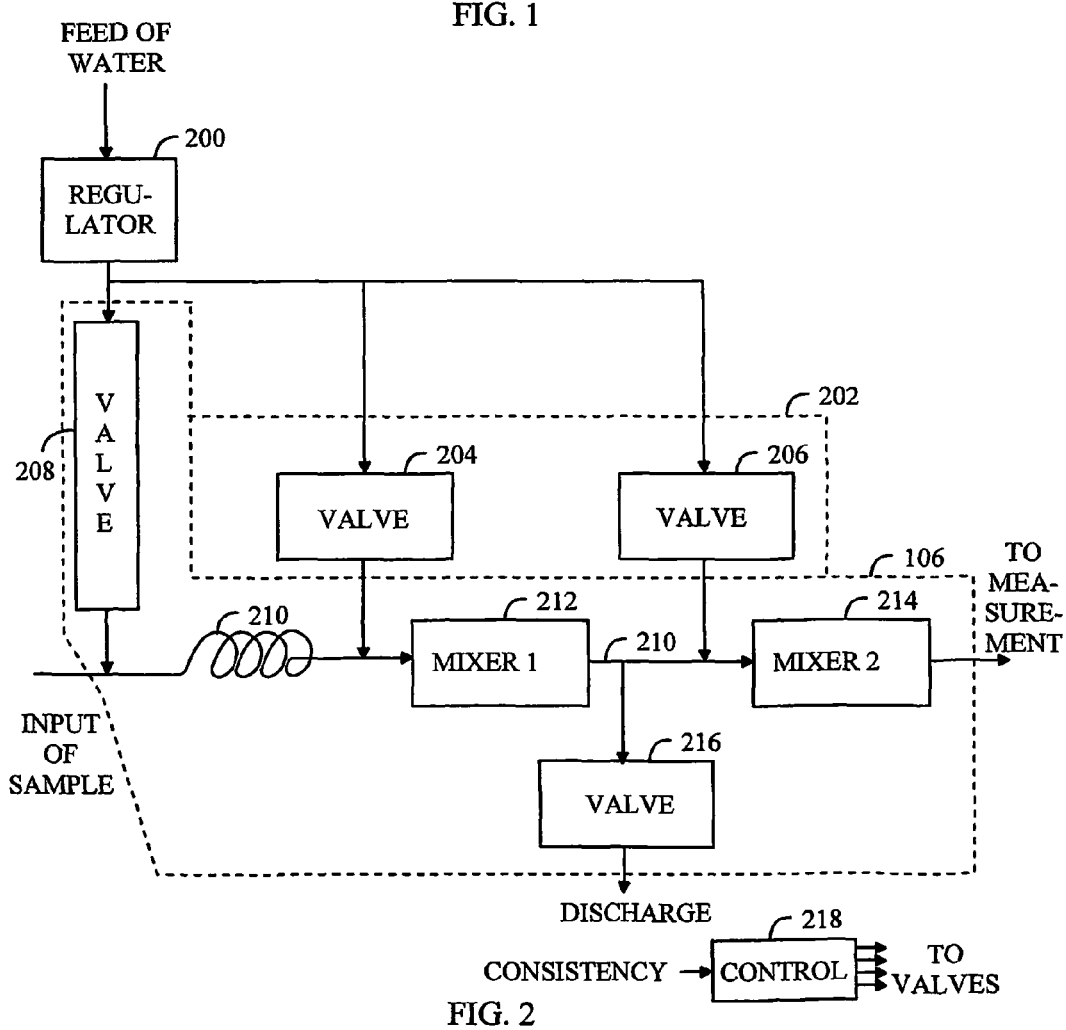
Figure 3:
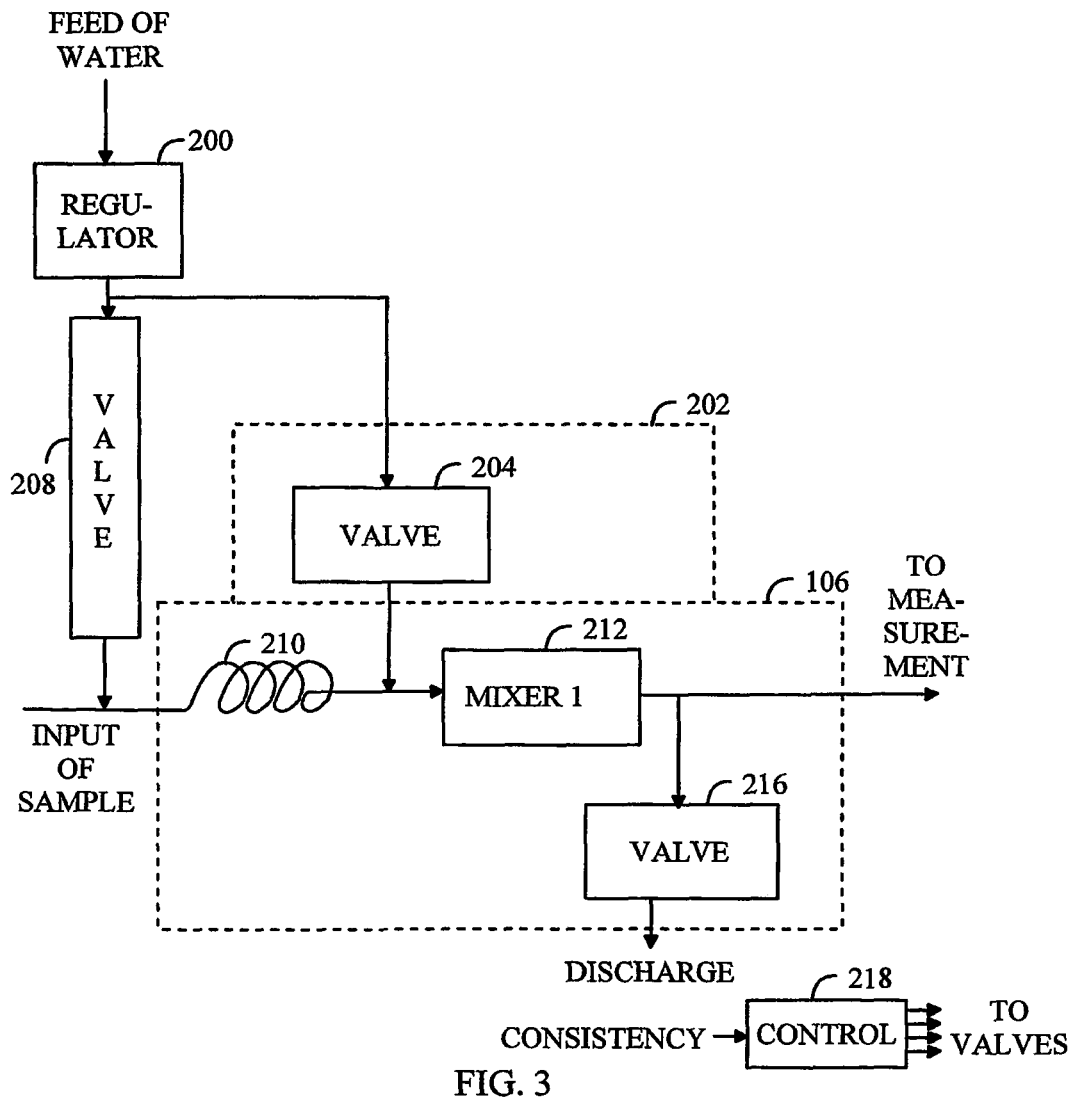
Figure 4A:
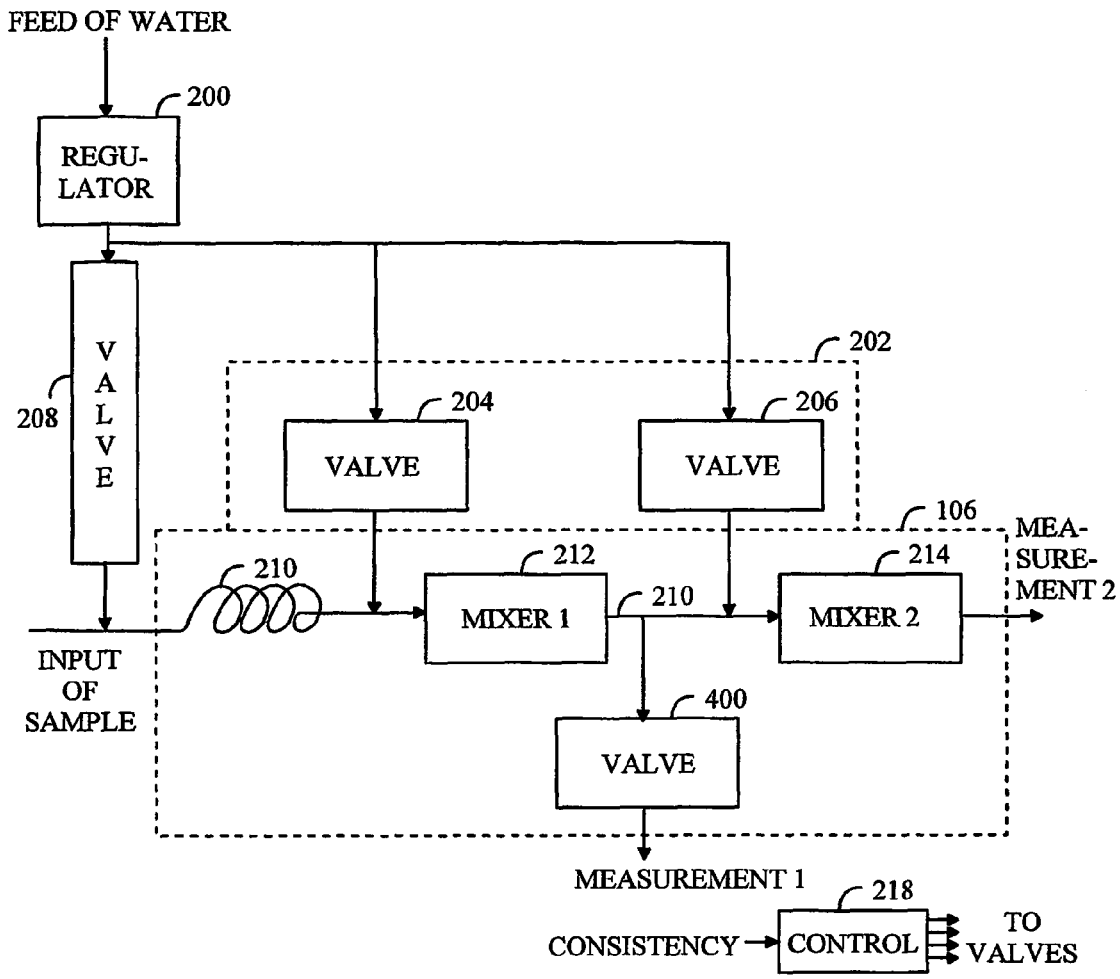
Figure 4B:
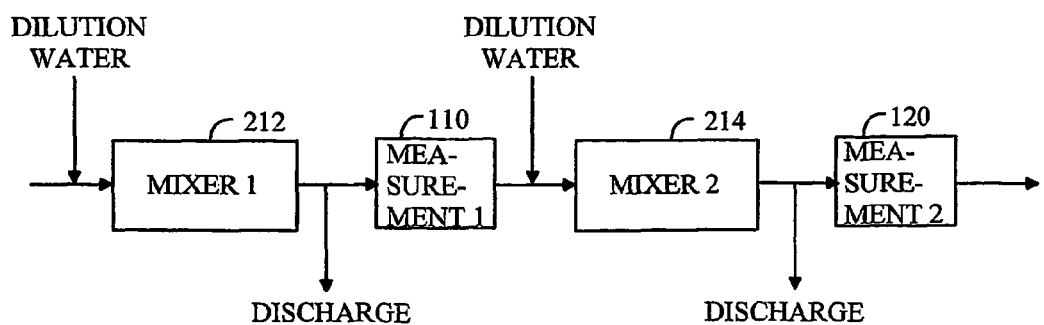
Figure 5:
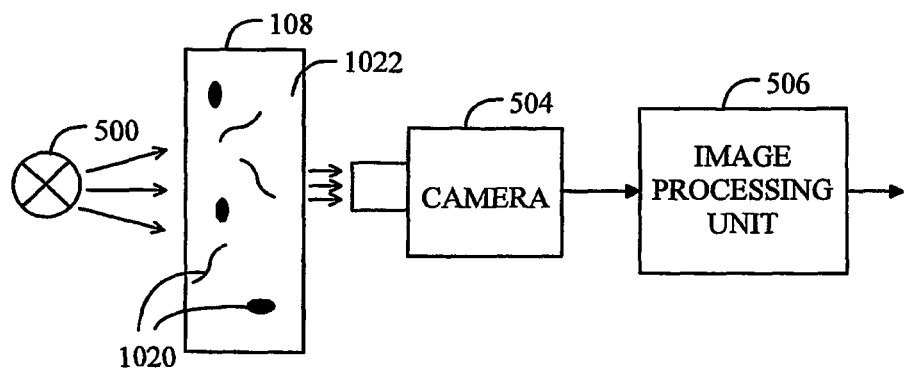
Figure 6:
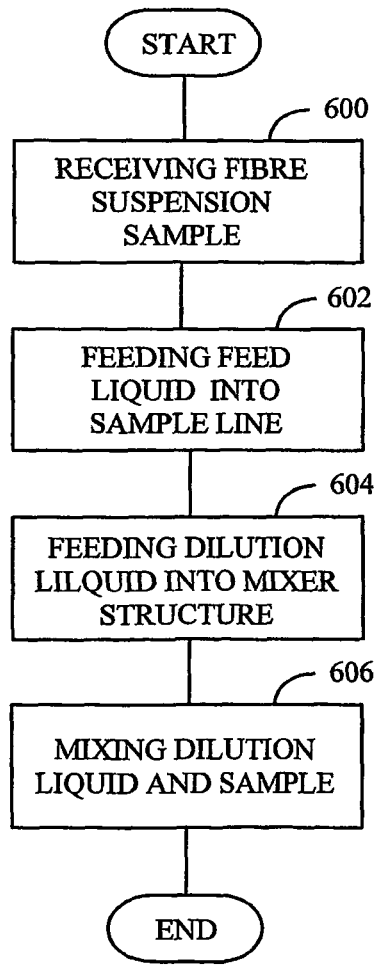
Figure 7:
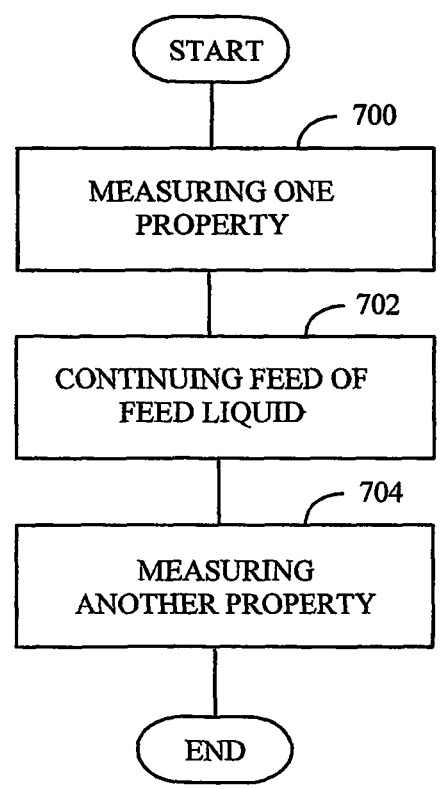

In the following the invention will be explained in greater detail by means of the preferred embodiments with reference to the accompanying drawings, in which FIG. 1 shows a measuring device, FIG. 2 shows a common mixer structure, FIG. 3 shows a mixer structure provided with one mixer, FIG. 4A shows mixing to be conducted in series, where measurements may be carried out in series or in parallel, FIG. 4B shows mixing to be conducted in series, where measurements are carried out in series, FIG. 5 shows a measuring unit, FIG. 6 is a block diagram showing a mixing method, and FIG. 7 is a block diagram showing a measuring method.

DESCRIPTION OF EMBODIMENTS

Let us first take a closer look at a measuring device shown in FIG. 1. A sample consisting of fibre suspension may be taken from a process tube 100 or from another process part. The sample is conveyed through a valve 102 possibly to a pre-processing unit 104 of the sample, where the consistency of the sample and other properties can be measured and changed. The fibre suspension comprises a liquid medium including particles of a solid, such as fibres. The fibre may be any fibre, such as animal fibre, plant fibre, cellulose fibre or synthetic fibre. The medium is typically water but in a common case the medium may be some other liquid. In the wood-processing industry the fibre 100 is typically wood fibre. The consistency of the sample taken from the process tube may vary from a couple of per cents to several per cents or it may even be over ten per cent. The pre-processing unit 104 may reduce the consistency accurately to a desired level for instance below one per cent. After the pre-processing unit 104 the consistency may be for instance 0.3%.

However, the pre-processing unit 104 is not necessarily required. The sample, whose consistency is typically known at least at some accuracy is further conveyed to a mixer structure 106 of the measuring device by means of the feed liquid arriving from a liquid line. The feed liquid may refer to water but other liquids can also be used. The feed liquid allows forwarding the sample successfully, since the sample acts like a plug in the tube of the sample line that moves inside the tube in front of the feed liquid without being mixed with the feed liquid. The feed liquid flow can be adjusted such that the sample moves at a desired rate in the sample line. In the mixer structure 106 the consistency of the sample can be reduced by mixing dilution liquid and the sample with one another. The dilution liquid may also refer to water but other liquids are also possible. If the consistency of the dilution liquid arriving at the mixer structure is known, then a desired amount of dilution liquid can be mixed with the sample, in which case the consistency of the sample may be reduced to the desired level in the mixer structure 106. The consistency of the sample can be set at for instance 0.015%. The flow of the dilution liquid can be adjusted such that a desired amount of water is mixed with the sample in order to achieve the desired consistency or change in consistency.

The sample is driven forward in the sample line using the water arriving from the water line. When an appropriate consistency of the sample is achieved in the mixer structure 106, the sample or a part thereof is pushed using the feed liquid to a measuring unit 108, where the sample or a part thereof is measured. The measured sample is removed and the measurement results are fed forward for instance to a controller controlling the process. In addition the measurement results can be shown on a display and/or printed on paper. The measuring device may comprise several sample lines, whereof each one may comprise the mixer structure and the measuring unit.

Let us take a closer look at the mixer structure shown in FIG. 2. A regulator 200 can be connected to the water line or to another water supply system, from which feed liquid is fed to convey the sample in the sample line. The regulator balances the pressure and pressurizes the feed liquid and the dilution liquid to the same pressure. The water supply system may receive the feed liquid thereof from more than one water source.

This example solution shows a mixer structure 106, where two mixers 212, 214 are used. The mixers 212, 214 can be tubes provided at the inside thereof with throttle rings or with other parts impeding the flow. The mechanical parts impeding the flow cause swirls and turbulence to the flowing sample, which mix the sample and the dilution liquid. Dilution liquid is fed into the mixers 212, 214 through mixing valves 204 and 206 included in the mixing valve structure 202, which may be separate valves or structurally fastened to one another. The mixing valves 204, 206 may refer to ON/OFF type of valves, which are either open or closed and not adjustable or valves in which the flow is adjustable. The controller 218 may control the flow travelling through the mixing valves 204, 206 such that a desired amount of water is mixed with the sample in order to achieve the desired consistency or change in consistency. In addition the feeding valve 208 may also be an ON/OFF type valve, which is either open or closed and not adjustable, or a valve in which the flow is adjustable. The feeding valve 208 can be used to adjust the flow of the feed liquid arriving from the water line or from another water supply system in the sample line, and the movement of the sample in the sample line is therefore manageable. For this purpose the controller 218 may control the flow travelling through the feeding valve 208 such that the sample moves at desired rate in the sample line.

The mixer structure 106 may be used to adjust the consistency, if the consistency is measured before or after the mixer structure 106 and the consistency information is fed into the controller 218. Thus by means of guiding the controller 218 may change the flow of the valves 204 to 208 in the sample line 210, which alters the consistency of the sample. The reduction of the consistency in the mixer structure 106 can be changed by accelerating the flow of the feed liquid from the feeding valve 208, in which case the faster the feed liquid flows the less the consistency of the sample is reduced, or by decelerating the flow of the feed liquid, in which case the slower the feed liquid flows the more the consistency of the sample is reduced. Reducing the consistency in the mixer structure 106 can be changed by accelerating the flow of the feed liquid, in which case the faster the dilution liquid flows the more the consistency of the sample is reduced, or by decelerating the flow of the dilution liquid, in which case the slower the dilution liquid flows the less the consistency of the sample is reduced.

Each mixing valve structure 202 and feeding valve 208 in the sample line may be connected to a water supply system provided substantially with the same pressure. Alternatively each mixing valve structure 202 and feeding valve 208 may be connected to the same water supply system. Furthermore, alternatively the mixing valve structure 202 and the feeding valve 208 may be connected to the water supply system provided with the same constant pressure.

Since samples can be taken from the process consecutively continuously, the sample line is to be adequately long in order to process the consecutive samples separately. The length of the sample line may therefore be dozens of meters, portrayed by a thread 210, and it may comprise a sample of a size holding liters. The sample line may be made of plastic or metal tube. A desired part may be removed from the sample in the mixer structure 106 through a discharge valve 216.

The sample can be processed as follows. The sample, which may hold for instance 2-3 liters, is allowed to proceed towards the mixer structure 106. The feeding valve 208 is opened and the sample is to be conveyed by the feed liquid arriving from the water line towards a first mixer 212. In order to add dilution liquid to the sample a mixing valve 204 is opened before the first mixer 212, in which the sample and the dilution liquid are mixed in order to reduce the consistency. The forward end of the sample can be guided through the discharge valve 216 from the mixer structure 106, since the forward end of the sample is not necessarily representative. The amount of sample to be removed may be for instance 10% to 20% of the total amount of the sample. The removed part of the sample can be guided back to the process or be discharged through drainage to waste treatment.

After this the sample can be conveyed towards a second mixer 214, before which dilution liquid may be fed into the sample line by opening the second mixing valve 206. In the same way as in the first mixer the dilution liquid and at least some of the sample are mixed in the second mixer 214 in order to reduce the consistency. In the first mixer 212 the consistency of the sample can be reduced for instance to a level of 0.015% and in the second mixer 214 at least some of the sample can be mixed to be more dilute, for instance to a consistency of 0.0025%.

When two mixers are used the measuring of the sample can be continued to the first part and to the second part. Also more mixers and mixing valves can be used but the operation thereof is not similar. In order to measure the first part of the sample the first part of the sample is conveyed using the feed liquid to the measuring unit 108. Hence, the forward part of the sample in the measuring unit 108 has a consistency that is formed in the second mixer 214. The measuring unit 108 measures at least one property from the sample, which may include for instance the amount and dimension of sticks. After this the part of the sample in the measuring unit is removed from the measuring unit 108 by pushing the sample forward. After having reduced the consistency the mixing valve structure may be used to reduce the feed of dilution liquid in order to increase the consistency. The mixing valve 206 can at this stage for instance be closed, in which case the sample taken from the process is not totally mixed with the consistency (e.g. 0.0025%) formed in the second mixer 214, instead the latter part of the sample remains at the consistency (e.g. 0.015%) formed in the first mixer 212. The latter part of the sample can be fed as a second part into the mixing unit 108, the consistency of the latter part being higher than that of the first part of the sample, and from the sample part provided with a higher consistency at least one further property can be measured, for instance the dimension of the fibres. The dimension may refer to the length, width, wall thickness, area etc. of the object.

Alternatively the consistency may be changed so that when the consistency of the sample is reduced by means of both mixers to the desired value (for instance at the level of 0.015%) and the first part of the sample is measured, the mixing valve structure may also be used to increase the feed of dilution liquid in order to further reduce the consistency. The mixing valve 206 may at this stage be opened for instance or the flow-through of the mixing valve 206 can be increased, in which case the consistency is further reduced (e.g. at the level of 0.0025%). The latter part of the sample can be fed as the second part to the measuring unit 108, the consistency of the latter part being lower than that of the first part, and from the sample part provided with the lower consistency at least one further property can be measured.

Instead of two or more mixers and two or more mixing valves the mixer structure 106 may comprise only one mixer and the mixing valve structure 202 may comprise merely one mixing valve connected to the mixer (e.g. the mixer 212 and the mixing valve 204) as shown in FIG. 3. Thus, when the sample arrives at the sample line the sample is forwarded by the feed liquid towards the mixer 212. After having opened the mixing valve 204 the sample and the dilution liquid are mixed together in the mixer 212 in order to achieve the lower consistency level (e.g. 0.015% or 0.0025%). Also in this case the forward end of the sample, which may for instance be 10% to 20% of the total amount of the sample, can be washed through the discharge valve 216 in order to improve the representativeness of the sample or the forward end measurements can be left unobserved. After this, the sample or a part of the sample can be conveyed to the measuring unit 108, in which the sample is measured. The measurement may then be aimed at for instance measuring sticks or measuring a parameter describing the fibre size or at both of them.

FIGS. 4A and 4B illustrate mixing to be carried out in series. In FIG. 4A the measurements may be carried out in series or in parallel. The measurements are basically similar to those shown in FIG. 2. In the solution shown in FIG. 4A the sample is transferred after the first mixer 212 through a valve 400 to the first measurement. The mixing valves 204 and 206 can be kept open during the total propagation time of the sample in the sample line, whereby the mixers 212 and 214 reduce the consistency of the sample to the desired levels. After the first mixer 212 the sample is at the first consistency (e.g. 0.015%). When the valve 400 is closed the sample proceeds to the second mixer 214, which further reduces the consistency of the sample by means of the dilution liquid arriving through the mixing valve 206 (e.g. to the level of 0.0025%). The sample proceeds from the second mixer 214 to the measurement. Since the measurement is in serial mode measuring may be carried out in a single measuring unit 108.

In the solution shown in FIG. 4B the sample proceeds from the mixer 212 to the first measuring unit 108. Before the measuring unit 108 the forward end of the sample can be removed to a discharge duct or the measurements of the forward end may be left unobserved as shown in FIG. 3. After the measuring unit 108 the sample can further be diluted with the dilution liquid in the measuring unit 214, and thereafter the sample can be fed into the second measuring unit 120. In accordance with the example the consistency of the sample in the measuring unit 108 may be 0.015% and in the measuring unit 120 the consistency of the sample may be 0.0025%. Correspondingly, as prior to the measuring unit 108, the forward part of the sample can be removed before the measuring unit 120. The different properties of the sample can be measured in the measuring units 108 and 120.

Measuring the dimensions of the objects to be measured can be carried out for instance in accordance with FIG. 5. Optical radiation is directed from an optical radiation source 500 to the measuring unit 108, where for instance low-consistency suspension including wood fibers and/or sticks (the consistency may range from 0.02% to 0.003%, however, without being restricted to such consistencies) are considered as objects. What can also be considered as objects 1020 in addition to the fibers in all kinds of measurements are fines particles, sticks, waste, fillers. Generally various particles of solids, liquids or gaseous bodies may instead of the fiber suspension be dispersed to a liquid medium 1022.

The optical radiation source 500 may emit ultraviolet radiation, visible light or infrared radiation. A camera comprising a detecting pixel matrix that is liable to optical radiation may function as a detector 504. The pixel matrix may be a solid-state component, such as a CCD cell (Charge Coupled Device). When the optical radiation focused on the measuring unit 108 is removed from the measuring unit 108 the optical component forming the image, such as a lens or a combination of lenses, can be used to form the desired type of image from the mixture of particles and medium within the measuring unit 108 to the detector 504. The optical radiation source 500 and the detector 504 may be placed on opposite sides of the measuring unit 108, in which case the measuring unit 108 is transilluminated.

Each pixel in the detector 504 converts the strength of the optical signal hitting thereto to an electric signal. The electrical signals formed are converted to a digital image information signal, which is fed into an automatic image processing unit 506. The image processing unit 506 may carry out the measurements of the objects using the image processing program. The measurements may be aimed at the amount, length, thickness, wall thickness, area, waviness, fibrillation, fibre kinks, fibre cells, freeness, consistency, retention, kappa number, brightness, amount of alkali, dissolved lignin, HW/SW (hardwood-softwood ratio), pH-value, conductivity etc. Many of these measurements may be carried out in other modes than optically.

FIG. 6 is a flow chart showing a method for changing consistency. In step 600 the fibre suspension sample is received at least from one process part to at least one sample line. The following steps are carried out in each sample line, where in step 602 feed liquid is fed into the sample line for pushing the sample forward in the sample line. In step 604 dilution liquid is fed into the sample line. In step 606 the flowing sample and the dilution liquid are mixed with one another in order to reduce the consistency.

FIG. 7 is a flow chart showing a method for changing fibre suspension. Here, in addition to the method steps 600 to 606 for changing the consistency, steps are carried out where in step 700 at least one property of the wood fibre suspension is measured from a first part of the mixed sample when the sample arrives at the measuring unit. In step 702 feeding of feed liquid is continued for pushing the sample in the sample line towards the measuring unit. In step 704 a second part of the mixed sample is used to measure at least one further property of the wood fibre suspension.

The image processing unit 506 can be carried out as a processor including programs and the method shown can be implemented as a computer program. The image processing unit 506 can alternatively be implemented as an apparatus structure using separate logic components or one or more application-specific integrated circuits (ASIC). A combination of the different implementations is also possible.

In the solution shown the feeding valve of the water pushing the sample and each mixing valve are connected to the same water supply system. Consequently, the pressure variations do not affect the adjustment of the consistency. Since each mixing valve is arranged to feed water into the sample line before a corresponding mixer and also since the mixer is arranged to mix the flowing sample and the water fed from the mixing valve with each other, a desired amount of the sample at the desired consistency is rapidly provided, thus saving dilution liquid. Dilution liquid is saved especially when a representative part of the sample is measured before the consistency of the entire sample is reduced. This is due to the fact that as the consistency of the sample is reduced as a continuous process, the reduction of the consistency of the sample can be stopped when the measuring is carried out accurately and/or reliably enough.

In addition to the advantages previously presented in this application the measuring device is also easy to clean. Cleaning can be carried out as air cleaning or chemical cleaning. In air cleaning air can be directed at high pressure to the measuring unit and the sample line, in which case the water remained in the measuring unit or the sample line together with the forcefully flowing air mechanically cleans the dirt and the blockages. This operates particularly well in a tubular sample line and measuring unit. In chemical cleaning detergent is fed into the sample line and the measuring unit which releases and rinses the dirt and the blockages to the discharge duct. In this solution the dilution liquid intended to reduce the consistency and/or the feed liquid may also function as cleaning water.

Even though the invention has above been described with reference to the examples shown in the accompanying drawings it is apparent that the invention is not restricted thereto, but can be modified in various ways within the scope of the appended claims.

The invention claimed is:

1. An arrangement for changing the consistency of a sample including a fibre suspension, the arrangement comprising:
   at least one mixer structure comprising:
      a sample line;
      a feeding valve; and
      at least one mixer as a part of the sample line;
   at least one mixing valve structure comprising at least one mixing valve; and
   a measurement unit;
   wherein:
      the at least one mixer structure is configured to receive the sample comprising the fibre suspension, the sample having a predetermined consistency;
      the feeding valve is configured to feed a feed liquid into the sample line to move the sample forward in the sample line to the measurement unit through the at least one mixer;
      the at least one mixing valve structure is configured to feed a dilution liquid into the sample line;
      the at least one mixer in the sample line is configured to mix the forward moving sample and the dilution liquid together to change the consistency of the sample; and
      the measurement unit is configured to measure a consistency of the sample after the sample is moved through the at least one mixer.

2. A method for changing a consistency of a sample comprising a fibre suspension, the method comprising:
   inserting the sample into the arrangement according to claim 1; and
   changing the consistency of the sample in the at least one mixer.

3. The method according to claim 2, wherein the feed liquid and the dilution liquid are fed into the sample line at substantially the same pressure.

4. The method according to in claim 2, wherein the arrangement further comprises at least one controller configured to control:
   a rate of the forward movement of the sample through the sample line by controlling an operation of the feeding valve that feeds the feed liquid into the sample line to move the sample forward in the sample line; and an amount of the dilution liquid that is fed into the sample line by the mixing valve structure and mixed with the sample to achieve a certain consistency of the sample or a certain change in the consistency of the sample.

5. The method according to in claim 2, wherein the feeding valve is configured to change a reduction of the consistency of the sample in the mixer structure by:
   accelerating a flow of the feed liquid in the sample line to decrease the reduction of the consistency of the sample, or
   decelerating the flow of the feed liquid to increase the reduction of the consistency of the sample.

6. The method according to in claim 2, wherein the mixing valve structure is configured to change a reduction of the consistency of the sample by:
   accelerating a flow of the dilution liquid to increase the reduction of the consistency of the sample; or
   decelerating the flow of the feed liquid to decrease the reduction of the consistency of the sample.

7. The arrangement according to claim 1, wherein the mixing valve structure and the feeding valve are connected to a water supply system provided with the same pressure.

8. The arrangement according to claim 7, wherein the mixing valve structure and the feeding valve are connected to the same water supply system.

9. The arrangement according to claim 7, wherein the mixing valve structure and the feeding valve are connected to the same water supply system provided with a constant pressure.

10. The arrangement according to claim 1, further comprising at least one controller configured to control:
   a rate of the forward movement of the sample through the sample line by controlling an operation of the feeding valve that feeds the feeding liquid into the sample line to move the sample forward in the sample line; and
   an amount of the dilution liquid that is fed into the sample line by the mixing valve structure and mixed with the sample to achieve a certain consistency of the sample or a certain change in the consistency of the sample.

11. The arrangement according to claim 1, wherein the feeding valve is configured to change a reduction of the consistency of the sample by:
   accelerating a flow of the feed liquid in the sample line to decrease the reduction of the consistency of the sample; or
   decelerating the flow of the flow liquid to increase the reduction of the consistency of the sample.

12. The arrangement according to claim 1, wherein the mixing valve structure is configured to change a reduction of the consistency of the sample in the mixer structure by:
   accelerating a flow of the dilution liquid to increase the reduction of the consistency of the sample, or
   decelerating the flow of the dilution liquid to decrease the reduction of the consistency of the sample.

13. The arrangement according to claim 1, wherein after a reduction of the consistency of the sample, the mixing valve structure is configured to reduce the feed of the dilution liquid to the sample line to increase the consistency of the sample.

14. The arrangement according to claim 1, wherein:
   the at least one mixer structure comprises a first mixer and a second mixer;
   the at least one mixing valve structure comprises a first mixing valve and a second mixing valve;
   the first mixing valve is configured to feed the dilution liquid into the sample line before the first mixer and the second mixing valve is configured to feed the dilution liquid into the sample line before the second mixer; and
   after a reduction of the consistency, the second mixing valve is configured to reduce the feed of the dilution liquid to the sample line before the second mixer to increase the consistency of the sample.

15. A measuring device for measuring at least one property of a sample comprising a fibre suspension having at least two consistencies, the measuring device comprising:
   at least one measuring unit; and
   at least one mixer structure configured to receive the sample comprising the fibre suspension from at least one process part, the sample having a predetermined consistency, the at least one mixer structure comprising:
      a sample line;
      at least one mixer as part of the sample line;
      a feeding valve configured to feed a feed liquid into the sample line to move the sample forward in the sample line to the measuring unit; and
      a mixing valve structure configured to feed a dilution liquid into the sample line; and
   wherein:
      the at least one mixer is configured to mix the sample and the dilution liquid together to change the consistency of the sample;
      the measuring unit is configured to:
         measure at least one property of a first part of the mixed sample after the feed liquid has moved the first part of the mixed sample through the at least one mixer and into the measuring unit; and
         then measure at least one property of a second part of the mixed sample after the feed liquid has moved the second part of the mixed sample through the at least one mixer and into the measuring unit; and
      the at least one property comprises a consistency of the sample comprising the fibre suspension.

16. A method for measuring at least one property of a sample comprising a fibre suspension having at least two consistencies, the method comprising:
   inserting the sample into the measuring device according to claim 15; and
   measuring at least one property of a first part and a second part the sample comprising the fibre suspension.

17. The method according to claim 16, wherein:
   the mixer structure comprises a first mixer and a second mixer;
   the mixing valve structure comprises a first mixing valve and a second mixing valve;
   the first mixing valve is configured to feed the the dilution liquid into the sample line before the first mixer;
   the second mixing valve is configured to:
      feed the dilution liquid into the sample line before the second mixer; and
      reduce the feed of the dilution liquid into the sample line after the measuring of the first part of the sample to increase the consistency of the second part of the sample.

18. The method according to claim 16, wherein the at least one property of the sample comprises the consistency and one or more selected from the group consisting of: amount, length, thickness, wall thickness, area, waviness, fibrillation, fibre kinks, fibre cells, freeness, retention, kappa number, brightness, amount of alkali, dissolved lignin, hardwood-softwood ratio, pH-value, conductivity of fines particles, sticks, waste, fibre kinks of fillers and fibre cells.

19. The measuring device according to claim 15, wherein:
   the mixer structure comprises a first mixer and a second mixer;

the mixing valve structure comprises a first mixing valve and a second mixing valve;

the first mixing valve is configured to feed the dilution liquid into the sample line before the first mixer;

the second mixing valve is configured to:
- feed the dilution liquid into the sample line before the second mixer; and
- reduce the feed of the dilution liquid into the sample line after the measuring of the first part of the sample to increase the consistency of the second part of the sample; and the measuring unit is configured to measure the at least one property of the second part of the sample at a higher consistency than the first part of the sample.

20. The measuring device according to claim 15, wherein the at least one property of the sample comprises the consistency and one or more selected from the group consisting of: amount, length, thickness, wall thickness, area, waviness, fibrillation, fibre kinks, fibre cells, freeness, retention, kappa number, brightness, amount of alkali, dissolved lignin, hardwood-softwood ratio, pH-value, conductivity of fines particles, sticks, waste, fibre kinks of fillers and fibre cells.

* * * * *